United States Patent
Sato et al.

(10) Patent No.: US 12,318,460 B2
(45) Date of Patent: Jun. 3, 2025

(54) DENTAL POLYMERIZABLE COMPOSITION

(71) Applicant: GC Corporation, Shizuoka (JP)

(72) Inventors: Keita Sato, Tokyo (JP); Atsushi Fujimi, Tokyo (JP); Shogo Murakami, Tokyo (JP); Ayaka Fujimoto, Tokyo (JP)

(73) Assignee: GC Corporation, Shizuoka (JP)

( * ) Notice: Subject to any disclaimer, the term of this patent is extended or adjusted under 35 U.S.C. 154(b) by 567 days.

(21) Appl. No.: 17/753,492

(22) PCT Filed: Aug. 19, 2020

(86) PCT No.: PCT/JP2020/031325
§ 371 (c)(1),
(2) Date: Mar. 4, 2022

(87) PCT Pub. No.: WO2021/049268
PCT Pub. Date: Mar. 18, 2021

(65) Prior Publication Data
US 2022/0339079 A1 Oct. 27, 2022

(30) Foreign Application Priority Data
Sep. 13, 2019 (JP) .................. 2019-167006

(51) Int. Cl.
*A61K 6/889* (2020.01)
*A61K 6/61* (2020.01)
*A61K 6/77* (2020.01)

(52) U.S. Cl.
CPC ............ *A61K 6/889* (2020.01); *A61K 6/61* (2020.01); *A61K 6/77* (2020.01)

(58) Field of Classification Search
CPC ......... C03C 3/062; C03C 3/083; C03C 3/085; C03C 3/112; C03C 2201/40; C03C 4/0021; C08L 33/00–26; C08F 20/00–40; C08F 22/00–24; C08F 120/00–40; C08F 122/00–24; C08F 220/00–40; C08F 222/00–24; A61K 6/00–90
See application file for complete search history.

(56) References Cited

U.S. PATENT DOCUMENTS

| | | |
|---|---|---|
| 2002/0103272 A1 | 8/2002 | Klee et al. |
| 2002/0176826 A1 | 11/2002 | Klee et al. |
| 2005/0014861 A1* | 1/2005 | Qian .............. A61K 6/50 523/116 |
| 2006/0160919 A1 | 7/2006 | Brugger et al. |
| 2007/0004820 A1 | 1/2007 | Klee et al. |
| 2007/0122356 A1 | 5/2007 | Kessler et al. |
| 2012/0059083 A1 | 3/2012 | Tokui et al. |

FOREIGN PATENT DOCUMENTS

| | | |
|---|---|---|
| EP | 2979681 | 2/2016 |
| EP | 3111914 | 1/2017 |
| JP | H11-322526 | 11/1999 |
| JP | H11-343304 | 12/1999 |
| JP | 2003192518 A * | 7/2003 |
| JP | 2008-500292 | 1/2008 |
| JP | 2008-500980 | 1/2008 |
| JP | 2008-509106 | 3/2008 |
| JP | 2012-051856 | 3/2012 |

OTHER PUBLICATIONS

Partial machine translation of JP-2003192518-A (Year: 2003).*
1 International Search Report for PCT/JP2020/031325 mailed on Oct. 20, 2020.

* cited by examiner

*Primary Examiner* — Kregg T Brooks
(74) *Attorney, Agent, or Firm* — IPUSA, PLLC

(57) ABSTRACT

A dental polymerizable composition includes: a first agent including a (meth)acrylate having an acid group and an organic peroxide, and a second agent including a (meth)acrylate having no acid group, a thiourea derivative, and a glass powder, wherein the glass powder includes aluminum, silicon, and at least one of copper or vanadium.

3 Claims, No Drawings

DENTAL POLYMERIZABLE COMPOSITION

TECHNICAL FIELD

The present invention relates to a dental polymerizable composition.

BACKGROUND ART

In dental treatment, dental cement is used when attaching a prosthesis.

As a dental polymerizable composition, other than dental cement, a protective material for hypersensitivity, a pediatric sealant and the like are used.

As an example of the dental polymerizable composition, a two-agent dental polymerizable composition that includes a first agent including a (meth)acrylate having an acid group and an organic peroxide, and a second agent including a (meth)acrylate having no acid group, a thiourea derivative, a vanadium compound, and fluoroaluminosilicate glass powder is known (see, for example, Patent Literature 1).

CITATION LIST

Patent Literature

[PTL 1]
Japanese Laid-Open Patent Publication No. 2012-51856

SUMMARY OF INVENTION

Technical Problem

However, it has been desired to improve the curability of the two-agent dental polymerizable composition after long-term storage, that is, to improve the storage stability of the two-agent dental polymerizable composition.

One aspect of the present invention is intended to provide a two-agent dental polymerizable composition having excellent storage stability.

Solution to Problem

One aspect of the present invention includes: a dental polymerizable composition that includes a first agent including a (meth)acrylate having an acid group and an organic peroxide, and a second agent including a (meth)acrylate having no acid group, a thiourea derivative, and a glass powder, wherein the glass powder includes aluminum, silicon, and at least one of copper or vanadium.

Advantageous Effects of Invention

According to one aspect of the present invention, a two-agent dental polymerizable composition having excellent storage stability, can be provided.

DESCRIPTION OF EMBODIMENTS

In the following, embodiments of the present invention will be described.

Dental Polymerizable Composition

A dental polymerizable composition according to the present embodiment is a dental polymerizable composition that includes a first agent including a (meth)acrylate having an acid group and an organic peroxide, and a second agent including a (meth)acrylate having no acid group, a thiourea derivative, and a glass powder (hereinafter referred to as "glass powder") containing aluminum, silicon, and at least one of copper or vanadium.

The first agent may further include a (meth)acrylate having no acid group.

Examples of the properties of the first agent and the second agent include a paste and the like.

The mass ratio of the first agent and the second agent of the dental polymerizable composition according to the present embodiment is typically 10:1 to 1:10.

The dental polymerizable composition according to the present embodiment is typically used by kneading the first agent and the second agent. When the first agent and the second agent are kneaded, the (meth)acrylate having an acid group reacts with the glass powder to form a copper ion and/or a vanadium ion.

The dental polymerizable composition according to the present embodiment may be applied to dental cement, a protective material for hypersensitivity, a pediatric sealant, and the like.

Hereinafter, components that constitute the dental polymerizable composition according to the present embodiment will be described.

(Meth)Acrylate

As used herein and in the claims, (meth)acrylate means a compound having one or more (meth)acryloyloxy groups (for example, monomers, oligomers, and prepolymers). The (meth)acryloyloxy group means methacryloyloxy group and/or acryloyloxy group.

Examples of (meth)acrylates having an acid group include (meth)acrylates having a phosphate group, (meth)acrylates having a pyrophosphate group, (meth)acrylates having a thiophosphate group, (meth)acrylates having a carboxyl group, (meth)acrylates having a sulfonic acid group, (meth)acrylates having a phosphonic acid group, and the like. Two or more (meth)acrylates may be used in combination. Among these, (meth)acrylates having a phosphate group or (meth)acrylates having a thiophosphate group are preferable in terms of the adhesiveness of the dental polymerizable composition according to the present embodiment.

The (meth)acrylate having an acid group may have multiple acid groups.

For the (meth)acrylate having an acid group, acid chlorides, alkali metal salts, amine salts, and the like of the (meth)acrylate having an acid group may also be used.

Examples of (meth)acrylates having a phosphate group include 2-(meth)acryloyloxyethyldihydrogenphosphate, bis[2-(meth)acryloyloxyethyl]hydrogenphosphate, 2-(meth)acryloyloxyethylphenyl hydrogenphosphate, 6-(meth)acryloyloxyhexyldihydrogenphosphate, 6-(meth)acryloyloxyhexylphenyl hydrogenphosphate, 10-(meth)acryloyloxydecyldihydrogenphosphate, 1,3-di(meth)acryloylpropan-2-dihydrogenphosphate, 1,3-di(meth)acryloylpropan-2-phenylhydrogenphosphate, bis[5-{2-(meth)acryloyloxyethoxycarbonyl}heptyl] hydrogenphosphate, and the like. Among these, 10-methacryloyloxydecyldihydrogenphosphate is preferred in terms of the adhesiveness of the dental polymerizable composition according to the present embodiment.

Examples of (meth)acrylates having a pyrophosphate group include bis(2-(meth)acryloyloxyethyl) pyrophosphate, bis(4-(meth)acryloyloxybutyl) pyrophosphate, bis(6-(meth)acryloyloxyhexyl) pyrophosphate, bis(8-(meth)acryloyloxyoctyl) pyrophosphate, bis(10-(meth)acryloyloxydecyl) pyrophosphate, and the like.

Examples of (meth)acrylates having a thiophosphate group include 2-(meth)acryloyloxyethyldihydrogenthiophosphate, 3-(meth)acryloyloxypropyldihydrogenthiophosphate, 4-(meth)acryloyloxybutyldihydrogenthiophosphate, 5-(meth)acryloyloxypentyldihydrogenthiophosphate, 6-(meth)acryloyloxyhexyldihydrogenthiophosphate, 7-(meth)acryloyloxyheptyldihydrogenthiophosphate, 8-(meth)acryloyloxyoctyldihydrogenthiophosphate, 9-(meth)acryloyloxynonyldihydrogenthiophosphate, 10-(meth)acryloyloxydecyldihydrogenthiophosphate, 11-(meth)acryloyloxyundecyldihydrogenthiophosphate, 12-(meth)acryloyloxydodecyldihydrogenthiophosphate, 13-(meth)acryloyloxytridecyldihydrogenthiophosphate, 14-(meth)acryloyloxytetradecyldihydrogenthiophosphate, 15-(meth)acryloyloxypentadecyldihydrogenthiophosphate, 16-(meth)acryloyloxyhexadecyldihydrogenthiophosphate, 17-(meth)acryloyloxyheptadecyldihydrogenthiophosphate, 18-(meth)acryloyloxyoctadecyldihydrogenthiophosphate, 19-(meth)acryloyloxynonadecyldihydrogenthiophosphate, 20-(meth)acryloyloxyicosyldihydrogenthiophosphate, and the like.

Examples of (meth)acrylates having a carboxyl group include 4-(meth)acryloyloxyethyl trimellitic acid, 4-(meth)acryloyloxyethyl trimellitic anhydride, 4-(meth)acryloyloxydecyl trimellitic acid, 4-(meth)acryloyloxydecyl trimellitic anhydride, 11-(meth)acryloyloxy-1,1-undecanedicarboxylic acid, 1,4-di(meth)acryloyloxy pyromellitic acid, 2-(meth)acryloyloxyethylmaleic acid, 2-(meth)acryloyloxyethyl phthalic acid, 2-(meth)acryloyloxyethyl hexahydrophthalic acid, and the like.

Examples of (meth)acrylates having a sulfonic acid group include 2-(meth)acrylamide-2-methylpropanesulfonic acid, styrenesulfonic acid, 2-sulfoethyl (meth)acrylate, and the like.

Examples of (meth)acrylates having a phosphonic acid group include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and the like.

The content of the (meth)acrylate having an acid group in the dental polymerizable composition according to the present embodiment is preferably 0.1 to 20% by mass, and further preferably 0.5 to 10% by mass. When the content of the (meth)acrylate having an acid group in the dental polymerizable composition according to the present embodiment is 0.1% by mass or more, the adhesiveness of the dental polymerizable composition according to the present embodiment is further improved, and when the content is 20% by mass or less, the curability of the dental polymerizable composition according to the present embodiment is further improved.

Examples of (meth)acrylates having no acid group include methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methylhexyl (meth)acrylate, 2-ethylhexyl (meth)acrylate, benzyl (meth)acrylate, 2-hydroxy-1,3-di(meth)acryloyloxypropane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, polybutylene glycol di(meth)acrylate, bisphenol A diglycidyl (meth)acrylate, di-2-(meth)acryloyloxyethyl-2,2,4-trimethylhexamethylene dicarbamate, 1,3,5-Tris[1,3-bis{(meth)acryloyloxy}-2-propoxycarbonylaminohexane]-1,3,5-(1H,3H,5H)triazine-2,4,6-trione, 2,2-bis[4-(3-(meth)acryloyloxy-2-hydroxypropyl)phenyl]propane, N,N'-(2,2,4-trimethylhexamethylene)bis[2-(aminocarboxy)propane-1,3-diol]tetramethacrylate, and the like. Two or more (meth)acrylates may be used in combination. Among these, di-2-(meth)acryloyloxyethyl-2,2,4-trimethylhexamethylene dicarbamate, and 2-hydroxy-1,3-di(meth)acryloyloxypropane are preferable in terms of the mechanical strength of the cured product of the dental polymerizable composition according to the present embodiment.

The content of the (meth)acrylate having no acid group in the dental polymerizable composition according to the present embodiment is preferably 10 to 95% by mass, and further preferably 15 to 80% by mass. When the content of the (meth)acrylate having no acid group in the dental polymerizable composition according to the present embodiment is 10% by mass or more and 95% by mass or less, the handleability of the dental polymerizable composition according to the present embodiment is further improved.

Organic Peroxide

The organic peroxide functions as an oxidizing agent for a chemical polymerization initiator.

Examples of the organic peroxide include benzoyl peroxide, cumene hydroperoxide, t-butyl hydroperoxide, t-amyl hydroperoxide, 1,1,3,3-tetramethylbutyl hydroperoxide, 2,5-dimethyl-2,5-di(hydroperoxy)hexane, p-diisopropylbenzene monohydroperoxide, p-methane hydroperoxide, pinane hydroperoxide, and the like. Two or more organic peroxides may be used in combination. Among these, cumene hydroperoxide is preferable in terms of the curability of the dental polymerizable composition according to the present embodiment.

The content of the organic peroxide in the dental polymerizable composition according to the present embodiment is preferably 0.01 to 5% by mass, and further preferably 0.1 to 2% by mass. When the content of the organic peroxide in the dental polymerizable composition according to the present embodiment is 0.01% by mass or more, the curability of the dental polymerizable composition according to the present embodiment is further improved, and when the content is 5% by mass or less, the open time of the dental polymerizable composition according to the present embodiment is further increased.

Thiourea Derivative

The organic peroxide functions as a reducing agent for a chemical polymerization initiator.

Examples of the thiourea derivative include ethylene thiourea, N-methylthiourea, N-ethylthiourea, N-propylthiourea, N-butylthiourea, N-laurylthiourea, N-phenylthiourea, N-cyclohexylthiourea, N,N-dimethylthiourea, N,N-diethylthiourea, N,N-dipropylthiourea, N,N-dibutylthiourea, N,N-dilaurylthiourea, N,N-diphenylthiourea, N,N-dicyclohexylthiourea, trimethylthiourea, tetramethylthiourea, N-acetylthiourea, N-benzoylthiourea, 1-allyl-3-(2-hydroxyethyl)-2-thiourea, 1-(2-tetrahydrofurfuryl)-2-thiourea, N-tert-butyl-N'-isopropyithiourea, 2-pyridylthiourea, and the like. Two or more thiourea derivatives may be used in combination. Among these, N-benzoyl thiourea is preferable in terms of the curability of the dental polymerizable composition according to the present embodiment.

The content of the thiourea derivative in the dental polymerizable composition according to the present embodiment is preferably 0.1 to 5% by mass, and further preferably 0.2 to 1% by mass. When the content of the thiourea derivative in the dental polymerizable composition according to the present embodiment is 0.1% by mass or more, the curability of the dental polymerizable composition according to the present embodiment is further improved, and when the content is 5% by mass or less, the open time of the dental polymerizable composition according to the present embodiment is further increased.

Glass Powder

The glass powder functions as a reducing agent for a chemical polymerization initiator.

The content of silicon (Si) in the glass powder, when converted into the amount of silicon oxide ($SiO_2$), is preferably 20 to 50% by mass, and further preferably 25 to 40% by mass. When the content of silicon (Si) in the glass powder, when converted into the amount of silicon oxide ($SiO_2$), is 20% by mass or more, it is easier to make glass, and when the content is 50% by mass or less, the curability and the mechanical strength of the cured product of the dental polymerizable composition according to the present embodiment are further improved.

The content of copper (Cu) and/or vanadium (V) in the glass powder, when converted into the amount of copper oxide (CuO) and/or vanadium oxide ($V_2O_5$), is preferably 0.1 to 5% by mass, and further preferably 0.2 to 2% by mass. When the content of copper (Cu) and/or vanadium (V) in the glass powder, when converted into the amount of copper oxide (CuO) and/or vanadium oxide ($V_2O_5$), is 0.1% by mass or more, the storage stability of the dental polymerizable composition according to the present embodiment is further improved, and when the content is 5% by mass or less, coloring of the glass powder is suppressed so that the aesthetic of the dental polymerizable composition according to the present embodiment is further improved.

The content of aluminum (Al) in the glass powder, when converted into the amount of aluminum oxide ($Al_2O_3$), is preferably 20 to 40% by mass, and further preferably 25 to 35% by mass. When the content of aluminum (Al) in the glass powder, when converted into the amount of aluminum oxide ($Al_2O_3$), is 20% by mass or more, the curability of the dental polymerizable composition according to the present embodiment is further improved, and when the content is 40% by mass or less, the transparency of the glass powder is further improved.

The glass powder preferably further includes fluorine.

The content of fluorine (F) in the glass powder is preferably 1 to 30% by mass, and further preferably 3 to 20% by mass. When the content of fluorine (F) in the glass powder is 1% by mass or more, the open time of the dental polymerizable composition according to the present embodiment is further increased, and when the content is 30% by mass or less, the curability of the dental polymerizable composition according to the present embodiment is further improved.

The glass powder may further include strontium, phosphorus, lithium, and the like.

The content of strontium (Sr) in the glass powder, when converted into the amount of strontium oxide (SrO), is preferably 15 to 40% by mass, and further preferably 20 to 35% by mass. When the content of strontium (Sr) in the glass powder, when converted into the amount of strontium oxide (SrO), is 15% by mass or more, the X-ray contrast of the glass powder is further improved, and when the content is 40% by mass or less, the increase in the refractive index of the glass powder is suppressed so that the aesthetic of the dental polymerizable composition according to the present embodiment is further improved.

The content of phosphorus (P) in the glass powder, when converted into the amount of phosphorus oxide ($P_2O_5$), is preferably 0.1 to 15% by mass, and further preferably 1 to 5% by mass. When the content of phosphorus (P) in the glass powder, when converted into the amount of phosphorus oxide ($P_2O_5$), is 0.1% by mass or more, the handleability of the dental polymerizable composition according to the present embodiment is further improved, and when the content is 15% by mass or less, the curability of the dental polymerizable composition according to the present embodiment is further improved.

The content of lithium (Li) in the glass powder, when converted into the amount of lithium oxide ($Li_2O$), is preferably 9% by mass or less, and further preferably 5% by mass or less. When the content of lithium (Li) in the glass powder, when converted into the amount of lithium oxide ($Li_2O$), is 9% by mass or less, the curability of the dental polymerizable composition according to the present embodiment is further improved.

The median diameter of the glass powder is preferably 0.02 to 20 μm, and further preferably 0.02 to 10 μm. When the median diameter of the glass powder is 0.02 μm or more, the handleability of the dental polymerizable composition according to the present embodiment is further improved, and when the median diameter is 20 μm or less, the abrasion resistance of the cured product of the dental polymerizable composition according to the present embodiment is further improved.

The content of the glass powder in the dental polymerizable composition according to the present embodiment is preferably 4 to 90% by mass, and further preferably 15 to 80% by mass. When the content of the glass powder in the dental polymerizable composition according to the present embodiment is 4% by mass or more, the curability of the dental polymerizable composition according to the present embodiment is further improved, and when the content is 90% by mass or less, the handleability of the dental polymerizable composition according to the present embodiment is further improved.

Method for Producing Glass Powder

The glass powder can be produced by melting a raw material composition containing an aluminum compound, a silicon compound, a copper compound and/or a vanadium compound, and then pulverizing the raw material composition.

Examples of the aluminum compound include aluminum oxide, aluminum hydroxide, aluminum chloride, aluminum nitrate, and aluminum sulfate, and the like. Two or more aluminum compounds may be used in combination.

Examples of the silicon compound include silicic acid anhydride and the like. Two or more silicon compounds may be used in combination.

Examples of the copper compound include copper (II) acetylacetonate, copper (II) acetate, copper (II) chloride, copper (II) benzoate, copper (II) naphthenate, copper (II) bis(1-phenylpentan-1,3-dione) complex (copper (II) procetonate), copper (II) bissalicylate, copper (I) thiourea complex, copper (II) ethylenediamine tetraacetate complex, and the like. Two or more copper compounds may be used in combination.

The vanadium compound is preferably IV-valent or V-valent.

Examples of the IV-valent or V-valent vanadium compound include vanadium (IV) dioxide, vanadyl acetylacetonate, vanadyl acetylacetonate (IV), vanadyl oxalate (IV), vanadyl sulfate (IV), oxobis(1-phenyl-1,3-butanedionate) vanadium (IV), bis(maltolato)oxovanadium (IV), vanadium (V) pentoxide, sodium metavanadate (V), ammonium metavanadate (V), and the like. Two or more vanadium compounds may be used in combination.

The raw material composition may further include a fluorine compound, a strontium compound, a phosphorus compound, a lithium compound, and the like.

Examples of the fluorine compound include calcium fluoride, strontium fluoride, aluminum fluoride, sodium fluoride, and the like. Two or more fluorine compounds may be used in combination.

Examples of the strontium compound include strontium fluoride, strontium hydroxide, strontium carbonate, strontium oxide, strontium phosphate, and the like. Two or more strontium compounds may be used in combination.

Examples of the phosphorus compound include aluminum phosphate, aluminum hydrogen phosphate, calcium phosphate, strontium phosphate, sodium dihydrogen phosphate, and the like. Two or more phosphorus compounds may be used in combination.

Each compound contained in the raw material composition may be formulated so as to correspond to the composition of the glass powder.

Other Ingredient

The second agent may further include a vanadium compound, a tertiary amine, a photopolymerization initiator, a filler other than the glass powder, a polymerization inhibitor, and the like. The first agent may further include a filler other than the glass powder, a polymerization inhibitor, and the like.

The vanadium compound functions as a reducing agent for a chemical polymerization initiator.

Examples of the vanadium compound include oxovanadium oxalate, vanadyl acetylacetonate, vanadium acetylacetonate, vanadyl stearate, vanadium naphthenate, vanadium benzoyl acetonate, and the like. Two or more vanadium compounds may be used in combination. Among these, vanadyl acetylacetonate is preferable in terms of curability of the dental polymerizable composition according to the present embodiment.

The tertiary amine functions as a reducing agent for a chemical polymerization initiator.

The tertiary amine may be either a tertiary aliphatic amine or a tertiary aromatic amine. The tertiary amine is preferably a tertiary aromatic amine, and particularly preferably alkyl p-dialkylaminobenzoate.

Examples of the tertiary aliphatic amine include N,N-dimethylaminoethylmethacrylate, triethanolamine, and the like.

Examples of the alkyl p-dialkylaminobenzoate include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, propyl p-diethylaminobenzoate, and the like.

Examples of the tertiary aromatic amine other than the alkyl p-dialkylaminobenzoate include 7-dimethylamino-4-methylcoumarin, N,N-dimethylaniline, N,N-dibenzylaniline, N,N-dimethyl-p-toluidine, N,N-diethyl-p-toluidine, N,N-bis(2-hydroxyethyl)-p-toluidine, N,N,2,4,6-pentamethylaniline, N,N,2,4-tetramethylaniline, N,N-diethyl-2,4,6-trimethylaniline, and the like.

The tertiary amine may be used alone, or two or more tertiary amines may be used in combination.

Examples of the photopolymerization initiator include camphorquinone, phenylbis(2,4,6-trimethylbenzoyl)phosphine oxide, 2,4,6-trimethylbenzoyl diphenylphosphine, benzyl ketal, diacetyl ketal, benzyl dimethyl ketal, benzyl diethyl ketal, benzyl bis(2-methoxyethyl) ketal, 4,4'-dimethyl (benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyithioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylaminophenyl)ketone, 4,4'-bis(diethylamino)benzophenone, and the like. Two or more photopolymerization initiators may be used in combination.

Examples of the filler other than the glass powder described below include silicic acid anhydride powder, fumed silica, alumina powder, barium glass powder, fluoroaluminosilicate glass powder, and the like. Two or more fillers may be used in combination.

The filler other than the glass powder described below may be treated with a surface treatment agent such as a silane coupling agent.

Examples of the polymerization inhibitor include dibutyl hydroxytoluene, 6-tert-butyl-2,4-xylenol, 2,6-di-tert-butyl-p-cresol, and the like. Two or more polymerization inhibitors may be used in combination.

EXAMPLE

Hereinafter, examples of the present invention will be described. The present invention is not limited to the described examples.

Production of Glass Powders 1 to 7

Silicic acid anhydride ($SiO_2$), aluminum oxide ($Al_2O_3$), strontium fluoride ($SrF_2$), aluminum fluoride ($AlF_3$), aluminum hydrogen phosphate ($Al_2(HPO_4)_3$), vanadyl acetylacetonate, vanadium oxide ($V_2O_5$), and copper acetylacetonate were blended in a predetermined ratio. Using a mortar, the mixture was thoroughly mixed and stirred. The resulting mixture was placed in a platinum crucible, and the platinum crucible was placed in an electric furnace. The electric furnace was heated to 1350° C. so that the mixture was melted and homogenized sufficiently. The mixture was then flowed into water to obtain a bulk glass. The bulk glass was crushed using a vibration mill. The crushed glass was then wet milled for 20 hours using an alumina ball mill, and dried to yield Glass Powders 1 to 7.

The median diameter and composition of the glass powders were then analyzed.

Median Diameter of Glass Powder

A laser diffraction scattering particle size distributor LA-950 (manufactured by Horiba, Ltd.) was used to measure the particle size distributions of Glass powders 1 to 7. The median diameters of Glass powders 1 to 7 were all approximately 4 μm.

Composition of Glass Powder

Glass powders 1 to 7 were analyzed, and the compositions were determined using a ZSX Primus II fluorescent X-ray analyzer (manufactured by Rigaku Corporation).

Table 1 illustrates the results of the analysis of the composition (% by mass) of the glass powders.

TABLE 1

|  | GLASS POWDER | | | | | | |
|---|---|---|---|---|---|---|---|
|  | 1 | 2 | 3 | 4 | 5 | 6 | 7 |
| $SiO_2$ | 29.4 | 29.1 | 26.9 | 29.4 | 29.1 | 26.9 | 29.2 |
| $Al_2O_3$ | 31.1 | 30.7 | 30.0 | 31.1 | 30.7 | 30.0 | 30.2 |
| SrO | 28.1 | 27.5 | 29.0 | 28.1 | 27.5 | 29.0 | 28.5 |
| F | 9.9 | 9.9 | 7.9 | 9.9 | 9.9 | 7.9 | 10.8 |
| $P_2O_5$ | 1.3 | 1.3 | 1.3 | 1.3 | 1.3 | 1.3 | 1.3 |
| $V_2O_5$ | 0.2 | 1.5 | 4.9 |  |  |  |  |
| CuO |  |  |  | 0.2 | 1.5 | 4.9 |  |
| TOTAL | 100.0 | 100.0 | 100.0 | 100.0 | 100.0 | 100.0 | 100.0 |

The contents of Si, Al, Sr, P, V, and Cu are the amounts converted into the amounts of $SiO_2$, $Al_2O_3$, SrO, $P_2O_5$, $V_2O_5$, and CuO, respectively.

Examples 1 to 9, Comparative Examples 1 to 4

Preparation of Paste 1

A methacrylate having no acid group, a methacrylate having an acid group, an organic peroxide, a filler, and a polymerization inhibitor were mixed in the formulation (% by mass) illustrated in Table 2, and Paste 1 was obtained.

Preparation of Paste 2

A methacrylate having no acid group, a thiourea derivative, a glass powder, a filler, a tertiary amine, a photopolymerization initiator, a polymerization inhibitor, and a vanadium compound were mixed in the formulation (% by mass) illustrated in Table 2, and Paste 2 was obtained.

The meanings of abbreviations in Table 2 are as follows.
GDMA: 2-hydroxy-1,3-dimethacryloyloxypropane
UDMA: di-2-methacrylcyloxyethyl-2,2,4-trimethylhexamethylene dicarbamate
MDP: 10-methacryloyloxydecyldihydrogenphosphate
CHP: cumene hydroperoxide
Silica powder 1: RAF1000 (manufactured by Tatsumori Ltd.)
Silica powder 2: Aerosil (registered trade mark) R812 (hydrophobic fumed silica) (manufactured by Nippon Aerosil Co., Ltd.)
IA: 6-tert-butyl-2,4-xylenol
VAA: vanadyl acetylacetonate
NBTU: N-benzoyl thiourea
EPA: Ethyl p-dimethylaminobenzoate
CQ: camphorquinone
TPO: 2,4,6-trimethylbenzoyl diphenylphosphine oxide The storage stabilities of Paste 1 and Paste 2 (two-agent dental polymerizable compositions) were then evaluated.

Storage Stability

An accelerated test was performed to evaluate the storage stability of the two-agent dental polymerizable compositions. Specifically, Paste 1 and Paste 2 were stored at 60° C. for 2 weeks, then Paste 1 and Paste 2 before and after the storage were kneaded at a mass ratio of 1:1. The curing time was measured according to ISO 4049:2009. The curing time was measured as follows. A test piece was prepared by filling a kneaded product of Paste 1 and Paste 2 into a polyethylene tube having an inner diameter of 4 mm and a height of 6 mm. A temperature change of the test piece was recorded using a thermocouple.

The criteria for determining the storage stability are as follows.
Excellent: The difference between the curing times before and after the storage is 60 seconds or less.
Good: The difference between the curing times before and after the storage is more than 60 seconds and 120 seconds or less.
Bad: The difference between the curing times before and after the storage is more than 120 seconds.

Table 2 illustrates the results of the evaluation of the storage stability of the two-agent dental polymerizable compositions.

TABLE 2

| | | | EXAMPLE | | | | | | | | | COMPARATIVE EXAMPLE | | | |
|---|---|---|---|---|---|---|---|---|---|---|---|---|---|---|---|
| | | | 1 | 2 | 3 | 4 | 5 | 6 | 7 | 8 | 9 | 1 | 2 | 3 | 4 |
| PASTE 1 | (METH)ACRYLATE HAVING NO ACID GROUP | GDMA | 20 | 20 | 20 | 20 | 20 | 20 | 20 | 20 | 20 | 20 | 20 | 20 | 20 |
| | | UDMA | 35 | 35 | 35 | 35 | 35 | 35 | 35 | 35 | 35 | 35 | 35 | 35 | 35 |
| | (METH)ACRYLATE HAVING ACID GROUP | MDP | 3 | 3 | 3 | 3 | 3 | 3 | 3 | 3 | 3 | 3 | 3 | 3 | 3 |
| | ORGANIC PEROXIDE | CHP | 1 | 1 | 1 | 1 | 1 | 1 | 1 | 1 | 1 | 1 | 1 | 1 | 1 |
| | FILLER | SILICA POWDER 1 | 38.95 | 38.95 | 38.95 | 38.95 | 38.95 | 38.95 | 38.95 | 38.95 | 38.95 | 38.95 | 38.95 | 38.95 | 38.95 |
| | | SILICA POWDER 2 | 2 | 2 | 2 | 2 | 2 | 2 | 2 | 2 | 2 | 2 | 2 | 2 | 2 |
| | POLYMERIZATION INHIBITOR | IA | 0.05 | 0.05 | 0.05 | 0.05 | 0.05 | 0.05 | 0.05 | 0.05 | 0.05 | 0.05 | 0.05 | 0.05 | 0.05 |
| | TOTAL | | 100.00 | 100.00 | 100.00 | 100.00 | 100.00 | 100.00 | 100.00 | 100.00 | 100.00 | 100.00 | 100.00 | 100.00 | 100.00 |
| PASTE 2 | (METH)ACRYLATE HAVING NO ACID GROUP | GDMA | 17 | 17 | 17 | 17 | 17 | 17 | 17 | 17 | 17 | 17 | 17 | 17 | 17 |
| | | UDMA | 17 | 17 | 17 | 17 | 17 | 17 | 17 | 17 | 17 | 17 | 17 | 17 | 17 |
| | VANADIUM COMPOUND | VAA | | | | | | | 0.02 | 0.05 | 0.10 | | 0.02 | 0.05 | 0.10 |
| | THIOUREA DERIVATIVE | NBTU | 0.5 | 0.5 | 0.5 | 0.5 | 0.5 | 0.5 | 0.5 | 0.5 | 0.5 | | 0.5 | 0.5 | 0.5 |
| | GLASS POWDER | 1 | 63.20 | | | | | | | | | | | | |
| | | 2 | | 63.20 | | | | | | | | | | | |
| | | 3 | | | 63.20 | | | | | | | | | | |
| | | 4 | | | | 63.20 | | | | | | | | | |
| | | 5 | | | | | 63.20 | | | | | | | | |
| | | 6 | | | | | | 63.20 | | | | | | | |
| | | 7 | | | | | | | 63.18 | 63.15 | 63.10 | | | | |
| | FILLER | SILICA POWDER 2 | 2 | 2 | 2 | 2 | 2 | 2 | 2 | 2 | 2 | 63.20 | 63.18 | 63.15 | 63.10 |
| | | | | | | | | | | | | 2 | 2 | 2 | 2 |
| | TERTIARY AMINE | EPA | 0.15 | 0.15 | 0.15 | 0.15 | 0.15 | 0.15 | 0.15 | 0.15 | 0.15 | 0.15 | 0.15 | 0.15 | 0.15 |
| | PHOTOPOLYMERIZATION INITIATOR | CQ | 0.05 | 0.05 | 0.05 | 0.05 | 0.05 | 0.05 | 0.05 | 0.05 | 0.05 | 0.05 | 0.05 | 0.05 | 0.05 |
| | | TPO | 0.05 | 0.05 | 0.05 | 0.05 | 0.05 | 0.05 | 0.05 | 0.05 | 0.05 | 0.05 | 0.05 | 0.05 | 0.05 |
| | POLYMERIZATION INHIBITOR | IA | 0.05 | 0.05 | 0.05 | 0.05 | 0.05 | 0.05 | 0.05 | 0.05 | 0.05 | 0.05 | 0.05 | 0.05 | 0.05 |
| | TOTAL | | 100.00 | 100.00 | 100.00 | 100.00 | 100.00 | 100.00 | 100.00 | 100.00 | 100.00 | 100.00 | 100.00 | 100.00 | 100.00 |
| STORAGE STABILITY | CURING TIME BEFORE STORAGE | | 8'30" | 6'15" | 4'00" | 9'30" | 8'10" | 5'50" | 5'10" | 4'00" | 2'45" | 11'20" | 8'50" | 6'00" | 4'25" |
| | CURING TIME AFTER STORAGE | | 8'50" | 6'35" | 4'10" | 10'00" | 8'35" | 6'05" | 6'30" | 5'15" | 4'05" | 14'40" | 12'15" | 8'50" | 6'35" |
| | DETERMINATION | | EXCELLENT | EXCELLENT | EXCELLENT | EXCELLENT | EXCELLENT | EXCELLENT | GOOD | GOOD | GOOD | BAD | BAD | BAD | BAD |

From Table 2, it can be seen that the storage stabilities of the two-agent dental polymerizable compositions of Examples 1 to 9 are high.

In contrast, the storage stabilities of the two-agent dental polymerizable compositions of Comparative Examples 1 to 4 are low, because Paste 2 does not contain a glass powder containing copper or vanadium.

The present application claims priority to Japanese Patent Application No. 2019-167006, filed Sep. 13, 2019, with the Japanese Patent Office. The contents of which are incorporated herein by reference in their entirety.

The invention claimed is:

1. A dental polymerizable composition comprising:
   a first agent including a (meth)acrylate having an acid group and an organic peroxide, and
   a second agent including a (meth)acrylate having no acid group, a thiourea derivative, and a glass powder,
   wherein the glass powder includes aluminum, silicon, and vanadium, and
   wherein the second agent includes a tertiary amine.

2. The dental polymerizable composition according to claim 1, wherein a content of silicon in the glass powder, when converted into an amount of silicon oxide ($SiO_2$), is 20 to 50% by mass.

3. The dental polymerizable composition according to claim 1, wherein the glass powder further includes fluorine.

* * * * *